US012064243B2

United States Patent
Pei et al.

(10) Patent No.: US 12,064,243 B2
(45) Date of Patent: Aug. 20, 2024

(54) DISPOSABLE ELECTROCHEMICAL BIOSENSOR BASED ON NAD(P)-DEPENDENT DEHYDROGENASE AND DIAPHORASE

(71) Applicant: Nova Biomedical Corporation, Waltham, MA (US)

(72) Inventors: Jianhong Pei, Somerville, MA (US); Joseph Bedard, Waltham, MA (US); Aaron Tram, Weymouth, MA (US); Samantha Mosley, Hyde Park, MA (US); Chung Chang Young, Weston, MA (US)

(73) Assignee: NOVA BIOMEDICAL CORPORATION, Waltham, MA (US)

( * ) Notice: Subject to any disclaimer, the term of this patent is extended or adjusted under 35 U.S.C. 154(b) by 1058 days.

(21) Appl. No.: 16/747,720

(22) Filed: Jan. 21, 2020

(65) Prior Publication Data
US 2021/0219876 A1    Jul. 22, 2021

(51) Int. Cl.
*A61B 5/1486* (2006.01)
*C12N 9/02* (2006.01)
*G01N 27/327* (2006.01)

(52) U.S. Cl.
CPC .......... *A61B 5/1486* (2013.01); *C12N 9/0008* (2013.01); *G01N 27/3272* (2013.01); *C12Y 102/01059* (2013.01); *C12Y 106/05002* (2013.01)

(58) Field of Classification Search
CPC .............. A61B 5/14546; A61B 5/1486; C12N 9/0008; C12Y 102/01059; C12Y 106/05002; G01N 27/3272
See application file for complete search history.

(56) References Cited

U.S. PATENT DOCUMENTS

2007/0131549 A1 * 6/2007 Cai .................. G01N 33/66
204/403.02
2010/0270175 A1 * 10/2010 Pei .................. C12Q 1/006
204/403.14

FOREIGN PATENT DOCUMENTS

WO     WO-2017151952 A1 *   9/2017  ......... A61B 5/14865

OTHER PUBLICATIONS

Zhou et al., "Progress of Electrochemical Biosensors Based on Nicotinamide Adenine Dinucleotide (phosphate)-Dependent Dehydrogenases," Chinese Journal of Analytical Chemistry, vol. 37, Issue 4, 2009, pp. 617-623 (Year: 2009).*

* cited by examiner

*Primary Examiner* — Eric J Messersmith
(74) *Attorney, Agent, or Firm* — Hayes Soloway PC

(57) ABSTRACT

A disposable biosensor that includes a sensing surface having at least a working electrode portion and a reference electrode portion, a first reagent disposed on the working electrode portion containing a NAD(P)-dependent dehydrogenase, NAD(P)+, diaphorase, and an oxidized form of a redox mediator forming a working electrode, and a reference electrode material disposed on the reference electrode portion forming a reference electrode.

21 Claims, 8 Drawing Sheets

DISPOSABLE ELECTROCHEMICAL BIOSENSOR BASED ON NAD(P)-DEPENDENT DEHYDROGENASE AND DIAPHORASE

BACKGROUND OF THE INVENTION

1. Field of the Invention

The present invention relates generally to electrochemical biosensors. Particularly, the present invention relates to electrochemical biosensors that use dehydrogenase as a catalyst for the determination of various analytes.

2. Description of the Prior Art

There are many electrochemical sensors that measure various analytes including, but not limited to, glucose, glutamate, lactate, cholesterol, d-hydroxybutyrate, glycerol, malate, leucine, alcohol, and the like. Some of the electrochemical sensors are designed for liquid measurement and some are designed for gas measurement.

Those designed for liquid measurement typically include a working electrode, a reference electrode and an optional counter electrode and further involve the use of the respective oxidase as the catalyst for performing the analysis. For example, glucose oxidase is used when measuring glucose, glutamate oxidase is used when measuring glutamate, etc. In addition, a redox mediator in its reduced state is involved in the chemical reaction that transforms the redox mediator to its oxidized state to produce a current that is proportional to the quantity of the analyte being measured.

Those designed for gas measurement typically include a working (or sensing) electrode, a counter electrode, and usually a reference electrode. These electrodes are enclosed in a sensor housing in contact with a liquid electrolyte. The working electrode is on the inner face of a Teflon® membrane that is porous to gas, but impermeable to the electrolyte. For any gas to be detectable by an electrochemical sensor, the gas must be electroactive. The gas diffuses into the sensor and through the membrane to the working electrode. When the gas reaches the working electrode, an electrochemical reaction occurs; either an oxidation or reduction depending on the type of gas. For example, carbon monoxide may be oxidized to carbon dioxide, or oxygen may be reduced to water. An oxidation reaction results in the flow of electrons from the working electrode to the counter electrode through the external circuit.

Conversely, a reduction reaction results in flow of electrons from the counter electrode to the working electrode. This flow of electrons constitutes an electric current, which is proportional to the gas concentration. The electronics in an associated instrument detects and amplifies the current and scales the output according to the calibration. The instrument then displays the gas concentration in, for example, parts per million (ppm) for toxic gas sensors and percent volume for oxygen sensors. Most alcohols are also electroactive, meaning that they undergo a change of oxidation state, or the breaking or formation of chemical bonds, in a charge-transfer step. Considerable work has been done in the development of alcohol fuel cells, and several alcohol breath meters (i.e. breathalyzers) used by police agencies are based on electrochemical sensors.

Most breathalyzers use either fuel cell sensor technology or semiconductor oxide sensor technology to measure the blood alcohol content (BAC) in a person's blood. Fuel cell sensors rely on an electrochemical process that oxidizes the alcohol in a breath sample. The oxidization produces an electrical current that the breathalyzer measures to determine the BAC. The strength of the current corresponds to the volume of alcohol present in the sample. Semiconductor Oxide sensors use a tin-oxide substance to measure BAC. A tin dioxide sensor heats a steel mesh film with a heater coil, and when exhaled alcohol hits the heated film, the resistance is changed. The change in sensor resistance is measured as the change of the output voltage across the fixed or variable resistor. There is a direct relationship between the sensor resistance and alcohol concentration. Breathalyzers with semiconductor sensor technology are less accurate than those with fuel cell sensors, and they are less expensive.

SUMMARY OF THE INVENTION

Very little work has been done in the past to measure alcohol concentration in whole blood. As mentioned previously, the most common alcohol measurement technology has been in the breathalyzer industry. Although there has been mentioned in prior art the use of alcohol dehydrogenase to measure alcohol concentration in blood, the alcohol sensors are not practical for use in disposable sensors due to various disadvantages of such sensors. These disadvantages include sensor shelf life stability, response sensitivity, range of concentration, and the number of available redox mediators in reduced form. Sensor shelf life stability is not long enough for a commercial product without using more complicated storage requirements. The response sensitivity is lower so accuracy is compromised. The low end of the concentration range is also compromised.

The present invention is a disposable electrochemical biosensor based on NAD(P)-dependent dehydrogenase and diaphorase. Diaphorase is flavoprotein enzyme capable of oxidizing the reduced forms of NAD and NADP such as di- and tri-phosphopyridine nucleotides. Because diaphorase enzyme is included, the oxidized form of the redox mediator can be used. Various advantages are provided by using a redox mediator in its oxidized form. The use of a redox mediator in its oxidized form is more stable than its corresponding reduced form in the ambient environment, thus benefiting shelf life stability of disposable biosensors. Another advantage is the disposable biosensor will produce a more sensitive response. A further advantage is that the disposable biosensor is capable of measuring very low concentration of the analyte being measured. Still another advantage is there are more choices of redox mediators in their oxidation form than there is for redox mediators in their reduced form. Another advantage is the oxidized form of the redox mediator is more stable in the ambient environment than the reduced form of the redox mediator in the same environment. This advantage translates to disposable biosensors not requiring special storage requirements like those of disposable biosensors using the reduced form of the redox mediator in order to exhibit similar shelf life stability.

It is an object of the present invention to provide a disposable biosensor for use with whole blood that has good shelf life stability without requiring special storage conditions.

It is another object of the present invention to provide a disposable biosensor for use with whole blood that has a more sensitive response than conventional disposable biosensors.

It is a further object of the present invention to provide a disposable biosensor for use with whole blood that is capable of measuring very low concentrations of interested species/analytes.

The present invention achieves these and other objectives by providing disposable biosensor with a longer shelf life stability, a more sensitive response and the ability to measure very low concentration of an interested species/analyte.

In one embodiment of the present invention, the disposable biosensor includes a sensing surface having at least a working electrode and a reference electrode, a first reagent disposed on a working electrode portion containing a NAD(P)-dependent dehydrogenase, NAD(P)+, diaphorase, and an oxidized form of a redox mediator forming the working electrode, and a reference electrode material disposed on a reference electrode portion forming the reference electrode.

In another embodiment of the present invention, the disposable biosensor further includes a blank electrode and a second reagent disposed on a blank electrode portion containing NAD(P)+, diaphorase, an oxidized form of a redox mediator and no dehydrogenase forming the blank electrode.

In one embodiment of the present invention, the reference material for forming the reference electrode is one of Ag—AgCl or a reference matrix containing at least a chemically oxidizing reagent selected from the group consisting of a reduced form of a redox mediator, an oxidized form of a redox mediator and a mixture of a reduced form and an oxidized form of a redox mediator.

In one embodiment, the NAD(P)-dependent dehydrogenase is one of alcohol dehydrogenase, glutamate dehydrogenase, glucose dehydrogenase, lactate dehydrogenase, cholesterol dehydrogenase, D-3-hydroxybutyrate dehydrogenase, glycerol dehydrogenase, malate dehydrogenase, and leucine dehydrogenase.

In one embodiment, the oxidized form of the redox mediator includes metal compounds or organic redox compounds.

In one embodiment, the oxidized form of the redox mediator includes at least one of potassium ferricyanide, sodium ferricyanide, ferrocene and its derivatives, ruthenium compounds such as hexaammineruthenium(III) chloride and its derivatives, osmium complexes, 1,10-phenanthroline-5,6-dione, meldola's blue, Tetrathiafulvalene 7,7,8,8-tetracyanoquinodimethane, hydroquinone, dichlorophenoliondophenol, p-benzoquinone, o-phenylenediamine, and 3,4-dihydroxybenzaldehyde.

In one embodiment, the first reagent further includes a polymer, a surfactant and a buffer. In a further embodiment, the first reagent further includes an optional bulking reagent.

In one embodiment, the second reagent further includes a polymer, a surfactant and a buffer. In a further embodiment, the second reagent further includes an optional bulking reagent.

In another embodiment of the present invention, the disposable biosensor further includes a base layer made of an electrically-insulating material with at least two electrical circuits delineated thereon, a channel forming layer made of an electrically-insulating material disposed on the base layer, and a cover layer made of an electrically-insulating material disposed over the channel forming layer. Each of the at least two electrical circuits extends longitudinally along the base layer and each of the at least two circuits has an electrically-conductive contact pad formed at each of a base layer proximal end portion and a base layer distal end portion with an electrically-conductive trace electrically coupling the electrically-conductive contact pad at the base layer proximal end portion with the corresponding electrically-conductive pad at the base layer distal end portion. One electrically-conductive pad at the base layer distal end portion forms the working electrode and the other of the electrically-conductive pad at the base layer distal end portion forms the reference electrode. The channel forming layer has a slot that extends from a channel layer distal end a predefined distance sufficient to expose each electrically-conductive pad at the base layer distal end portion. The channel forming layer has a shorter length than the length of the base layer so that each electrically-conductive pad at the base proximal end portion is exposed. The cover layer disposed over the channel forming layer creates a sample chamber delineated by the slot of the channel forming layer. The cover layer has a vent opening spaced from a cover layer distal end where the vent opening at least partially communicates with the sample chamber.

In one embodiment, the disposable biosensor further includes a reagent holding layer between the base layer and the channel forming layer. The reagent holding layer has at least two through openings at a reagent holding layer distal end where one of the at least two through openings coincides with the working electrode and the other of the at least two through openings coincides with the reference electrode.

In one embodiment, the base layer has a third electrical circuit extending longitudinally along the base layer. The third electrical circuit has an electrically-conductive contact pad formed at each of the base layer proximal end portion and the base layer distal end portion with an electrically-conductive trace electrically coupling the electrically-conductive contact pad at the base layer proximal end portion with the corresponding electrically-conductive pad at the base layer distal end portion forming the bland electrode. The bland electrode is within the slot of the channel forming layer.

In one embodiment, the reagent holding layer has a third through opening where the third through opening coincides with bland electrode.

In one embodiment, a method of making a disposable biosensor based on NADP-dependent dehydrogenase and diaphorase is disclosed. The method includes providing a sensing surface having at least a working electrode portion and a reference electrode portion, disposing a first reagent on the working electrode portion and drying the first reagent forming a first electrode matrix creating a working electrode, and disposing a reference electrode material on the reference electrode portion forming a reference electrode. The first reagent contains a NAD(P)-dependent dehydrogenase, NAD(P)+, diaphorase, and an oxidized form of a redox mediator. The reference electrode material is one of Ag—AgCl or a reference electrode reagent containing at least a chemically oxidizing reagent selected from the group consisting of a reduced form of a redox mediator, an oxidized form of a redox mediator and a mixture of a reduced form and an oxidized form of a redox mediator and drying the reference electrode reagent forming a reference electrode matrix.

In another embodiment, forming the first reagent includes adding together a predefined amount of the NAD(P)-dependent dehydrogenase, a predefined amount of NAD(P)+, a predefined amount of diaphorase, and a predefined amount of an oxidized form of a redox mediator into a predefined amount of water.

In another embodiment, the method includes measuring 0.1 grams to 0.5 grams of the NAD(P)-dependent dehydrogenase, measuring 0.02 grams to 0.1 grams of the NADP+, measuring 0.02 grams to 0.5 grams of the diaphorase, measuring 0.1 grams to 0.5 grams of the oxidized form of a redox mediator, and adding the NAD(P)-dependent dehydrogenase, the NAD(P)+, the diaphorase, and the redox mediator to 10 milliliters of water.

In one embodiment, the method includes measuring 0.2 grams to 0.4 grams of the NAD(P)-dependent dehydrogenase, measuring 0.05 grams of the NADP+, measuring 0.05 grams to 0.2 grams of the diaphorase, measuring 0.3 grams of the oxidized form of a redox mediator, and adding the NAD(P)-dependent dehydrogenase, the NAD(P)+, the diaphorase, and the redox mediator to 10 milliliter of water.

DETAILED DESCRIPTION OF THE INVENTION

Figure 1:
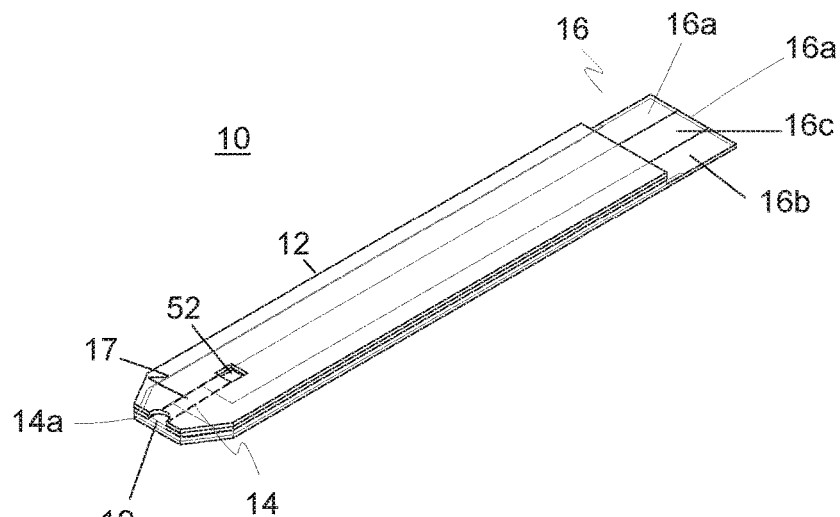
FIG. 1 is an enlarged, front perspective view of one embodiment of a disposable biosensor of the present invention.

The preferred embodiments of the present invention are illustrated in FIGS. 1-11. FIG. 1 illustrates one embodiment of the present invention. The disposable biosensor 10 is a multi-layered, integral biosensor having a laminated body 12, an electrode end portion 14, an electrode end 14a, an electrical contact end portion 16, an electrical contact end 16a, and a vent opening 52. Electrode end portion 14 includes a sample chamber 17 between a sample inlet 18 at electrode end 14a, and a vent opening 52. Electrical contact end portion 16 has at least three electrical coupling pads 16b, 16c and 16d that are in electrical contact with respective electrodes situated within sample test chamber 17. In this embodiment, disposable biosensor 10 has a length of 30 mm (1.2 inches) and a width of 5.5 mm (0.22 inches), however, such dimensions are non-limiting.

Figure 2:
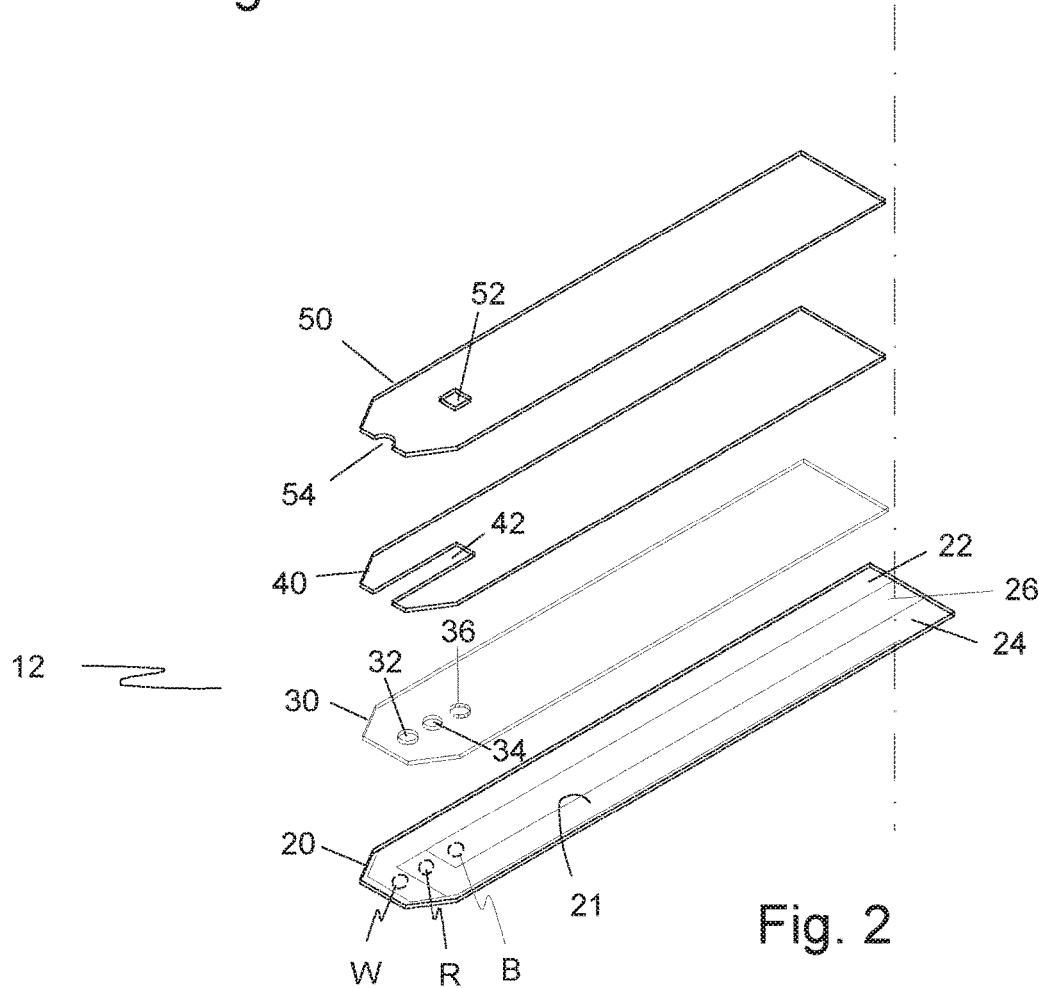
FIG. 2 is an exploded, perspective view of the disposable biosensor shown in FIG. 1.

Turning now to FIG. 2, laminated body 12 includes a base layer 20, a reagent holding layer 30, a channel forming layer 40, and a cover 50. All layers of laminated body 12 are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene, and polystyrene.

Base layer 20 has a conductive layer 21 on which is delineated three conductive paths 22, 24 and 26. The conductive paths 22, 24, 26 may be formed by scribing or scoring conductive layer 21. In the alternative, base layer 20 may be a dielectric material on which conductive paths 22, 24, 26 are silk screened. A piece of a gold polyester film may be used and cut to shape as illustrated in FIG. 2, forming base layer 20 of disposable biosensor 10.

Scribing or scoring of conductive layer 21 may be done by mechanically scribing the conductive layer 21 sufficiently to create the three independent conductive paths 22, 24, 26. The preferred scribing or scoring method of the present invention is done by using a carbon dioxide laser, a YAG laser or an excimer laser. The scoring line is very thin but sufficient to create the three separate electrical paths. Conductive layer 21 may be made of any electrically conductive material such as, for example, gold, tin oxide/gold, palladium, other noble metals or their oxides, or carbon film compositions. The preferred electrically conductive material is gold or tin oxide/gold. An additional scoring line 28 (enlarged and not to scale; for illustrative purposes only) may be made along the outer edge of base layer 20 where the conductive layer is removed in order to avoid possible static problems that could give rise to a noisy signal. It should be understood, however, that scoring line 28 is not necessary to the functionality of disposable biosensor 10. The preferred electrically conductive material for the base layer 20 is gold or tin oxide/gold coated polyester film.

Reagent holding layer 30 has a first electrode opening 32 which exposes a portion of first conductive path 22, a second electrode opening 34 which exposes a portion of second conductive path 24, and a third electrode opening 36 which exposes a portion of third conductive path 26. Reagent holding layer 30 is made of a plastic material, preferably a medical grade, one-sided adhesive tape available from Adhesive Research, Inc., of Glen Rock, PA or Global Instrument Corporation (GIC) (Taiwan). Acceptable thicknesses of the tape for use in the present invention are in the range of about 0.001 in. (0.025 mm) to about 0.005 in. (0.13 mm). The preferred thickness is about 0.003 in. (0.075 mm). It should be understood that the use of a tape is not required. Reagent holding layer 30 may be made from a plastic sheet and may be coated with a pressure sensitive adhesive, a photopolymer, ultrasonically-bonded to base layer 20, silk-screened onto the base layer 20, or 3D printed onto base layer 20 to achieve the same results as using the polyester tape mentioned.

The three electrode openings 32, 34 and 36 expose a portion of each conducting path 22, 24, 26, respectively, defining a working electrode portion 20W, a reference electrode portion 20R and a blank electrode portion 20B, that, in turn, define electrode wells W, R and B, respectively, and hold chemical reagents forming a working electrode (W), a reference electrode (R), and a blank electrode (B). Preferably, electrode well W is loaded with a NAD(P)-dependent dehydrogenase enzyme capable of catalyzing a reaction involving a substrate for the enzyme or a substrate catalytically reactive with the enzyme, a diaphorase, and an oxidized form of the mediator capable of transferring electrons transferred between the enzyme-catalyzed reaction and the working electrode to create a current representative of the activity of the enzyme or substrate (which is representative of the alcohol in the examples disclosed to be measured), and at least a polymer binder. Blank electrode well B is loaded with a similar chemistry to electrode well W, but without the dehydrogenase enzyme. One or more chemical components such as additional polymers, stabilizers, and bulking agents may be optionally included in the reagent matrix. A reference reagent matrix is loaded in electrode well R.

Preferably, the reference matrix contains at least a chemically oxidizing reagent such as a reduced form of a redox mediator, an oxidized form of redox mediator, or a mixture of a reduced and an oxidized form of a redox mediator. For example, potassium ferricyanide, or potassium ferrocyanide, or a mixture of potassium ferricyanide and potassium ferrocyanide may be loaded to make the reference electrode function when using the preferred conductive coating material. The mixture of potassium ferricyanide and potassium ferrocyanide may be prepared such that the potassium ferricyanide concentration is in the range of up to about 10%, while the potassium ferrocyanide concentration is in the range of up to about 5%. In the alternative, the reference electrode (electrode well R) may be loaded with a Ag/AgCl layer (e.g., by applying Ag/AgCl ink or by sputter-coating (a) a Ag layer followed by chloridizing the Ag or (b) a AgCl layer over a Ag layer) or other reference electrode materials that do not require a redox mediator to function properly. It should be noted that the positional arrangement of the working, the reference and the blank electrodes in the channel is not critical for obtaining usable results from the sensor.

The size of the reagent holding openings is preferred to be made as small as possible in order to make the sample chamber of the disposable biosensor as short as possible in order to minimize the volume of sample required for each test measurement. The three reagent holding/electrode openings 32, 34 and 36 are aligned with each other and are spaced about 0.02 in. (0.508 mm) to about 0.05 in. (1.27 mm) from each other. The circular reagent holding openings are for illustrative purposes only. It should be understood that the shape of the reagent holding openings and the distance between each of the electrodes is not critical. In fact, the reagent holding openings may differ in surface area from each other so long as the ratio of the surface areas remain substantially constant from one sensor to another.

The positional arrangement of the working, substrate and reference electrodes in the channel is not critical for obtaining usable results from the disposable biosensor. The possible electrode arrangements within the sample fluid channel may be W-B-R, W-R-B, R-W-B, B-W-R, B-R-W, or R-B-W, with the arrangement listed as the electrodes would appear from the sample inlet 18 of laminated body 12 to the vent opening 52. The preferred position was found to be W-R-B; that is, as the fluid sample enters sampling end 14 of laminated body 12, the fluid sample would cover the working electrode first, then the reference electrode, and then the blank electrode.

The three electrodes are each in electric contact with separate corresponding electrical coupling pads. The separate corresponding electrical coupling pads are exposed for making an electrical connection to a reading device.

Channel forming layer 40 has a channel notch 42 located at the electrode end portion 14. The length of channel notch 42 is such that when channel forming layer 40 is laminated to reagent holding layer 30, electrode areas W, R and B are within the space defined by channel notch 42. The length, width and thickness of the channel notch 42 define the capillary chamber volume. Channel-forming layer 40 is laminated to reagent holding layer 30. Like reagent holding layer 30, channel-forming layer 40 may be made from a plastic sheet and may be coated with a pressure sensitive adhesive, a photopolymer, ultrasonically-bonded to reagent holding layer 30, silk-screened onto the reagent holding layer 30, or 3D printed onto reagent holding layer 30.

Channel forming layer 40 is made of a plastic material, preferably a medical grade, double-sided pressure-sensitive adhesive tape available from Adhesive Research, Inc., of Glen Rock, PA or Global Instrument Corporation (Taiwan). The thickness of the tape is preferably in the range of about 0.001 in. (0.025 mm) to about 0.010 in. (0.25 mm). Channel notch 42 can be made with a laser or by die-cutting (the preferred method). The length of channel notch 42 is about 0.22 in. (5.7 mm) to about 0.250 in. (6.4 mm), the width is about 0.05 in. (1.3 mm) to about 0.07 in. (1.8 mm) and the thickness is about 0.0039 (0.1 mm) to about 0.009 in. (0.225 mm). It should be understood that the thickness and the size of channel notch 42 are not critical.

Cover 50, which is laminated to channel forming layer 40, has vent opening 52 spaced from electrode end 14a of disposable biosensor 10 to ensure that the sample in the sample chamber 17 will completely cover electrode areas W, R and B. Vent opening 52 is positioned in cover 50 so that it will expose a portion of and partially overlay channel notch 42 at or near the closed end of the channel notch 42. Vent opening 52 may be any shape but is illustrated as a rectangle having dimensions of about 0.08 in. (2 mm) by about 0.035 in. (0.9 mm). The preferred material for cover 50 is a polyester film. In order to facilitate capillary action of the sample fluid within the sample chamber 17, it is desirable for the polyester film to have a highly hydrophilic surface on that portion of the polyester film that forms the capillary chamber. Transparency films from 3M or from GIC can be used. Cover 50 may optionally include an inlet notch 54 to prevent an inadvertent occlusion of sample inlet 18 (which can prevent the proper transfer of the sample fluid to the electrodes) when applying a blood sample to sample chamber 17.

Figure 3:
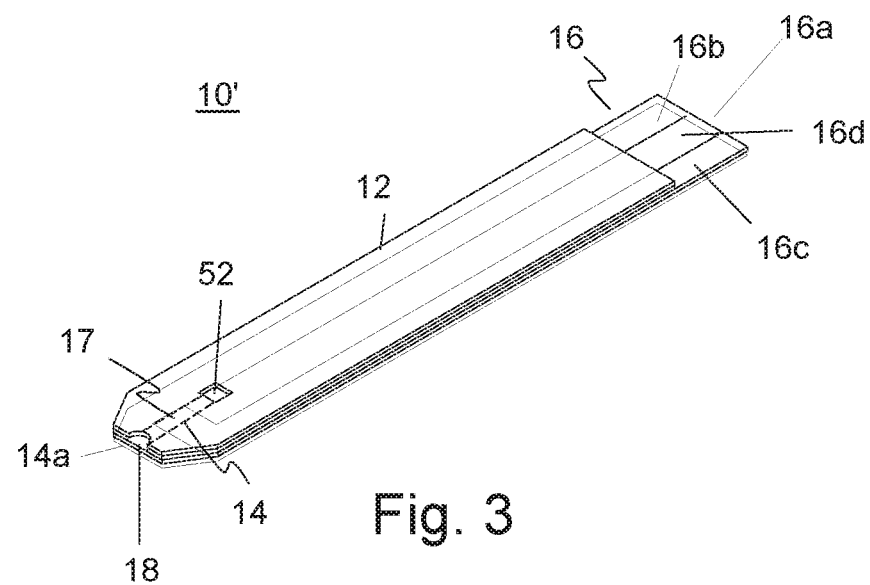
FIG. 3 is an enlarged, front perspective view of another embodiment of a disposable biosensor of the present invention.

FIG. 3 illustrates a 3-layer disposable biosensor 10'. Like the 4-layer embodiment, disposable biosensor 10' has a laminated body 12, an electrode end portion 14, an electrical contact end portion 16, and a vent opening 52. Electrode end portion 14 includes a sample chamber 17 between a sample inlet 18 and vent opening 52. Electrical contact end portion 16 has three discrete electrical coupling pads 16b, 16c and 16d.

Figure 4:
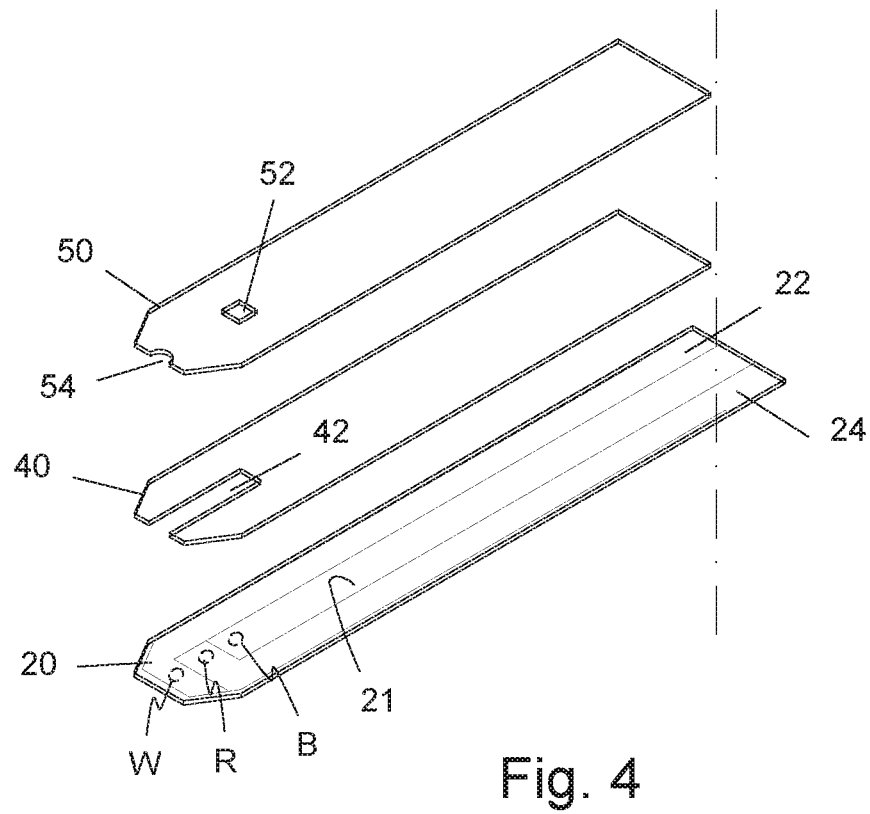
FIG. 4 is an exploded, perspective view of the disposable biosensor shown in FIG. 3.

As can be seen from FIG. 4, laminated body 12 includes a base layer 20, a channel forming layer 40, and a cover 50. As noted earlier, all layers of laminated body 12 are made of a dielectric material, preferably plastic. Unlike the 4-layer embodiment, there is no separate reagent holding layer in the 3-layer embodiment. Channel forming layer 40 also delineates the area in which a pre-determined amount of reagent mixtures are disposed onto the conductive paths as three distinct reagent matrix coatings on the working electrode, the reference electrode and the optional blank electrode, respectively.

Figure 5:
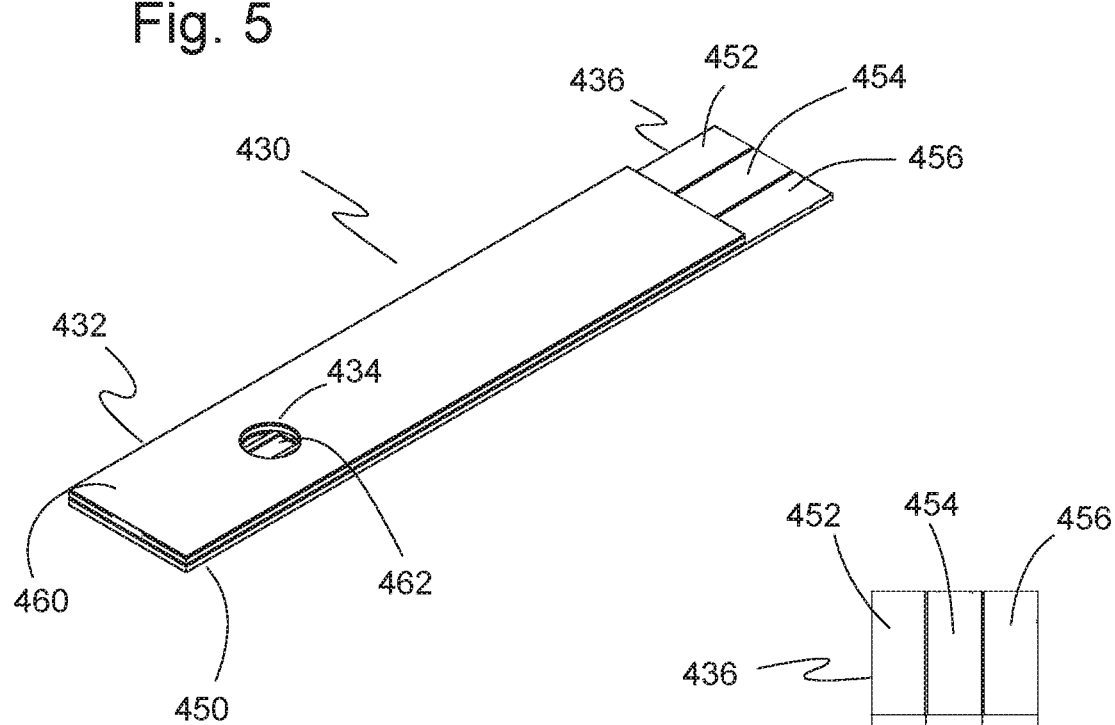
FIG. 5 is an enlarged, front, perspective view of another embodiment of a disposable biosensor of the present invention.
Figure 6:
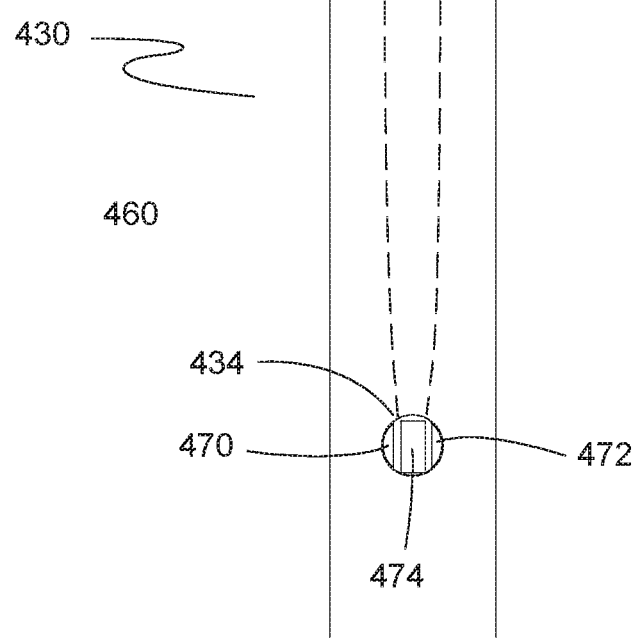
FIG. 6 is an enlarged, top plan view of the disposable biosensor shown in FIG. 5.

Turning now to FIG. 5, there is illustrated another embodiment of the present invention showing a disposable biosensor 430. Disposable biosensor 430 has a laminated body 432, a sample receiving well 434 and an electrical contact end 436. Laminated body 432 has a base layer 450 and a cover 460. Cover 460 has a sample opening 462 that forms, when combined with base layer 450, sample receiving well 434. Base layer 450 has at least three electrical paths 452, 454 and 456, which have a first portion exposed at electrical contact end 436 for connection to a meter device (not shown) and a second portion exposed by sample receiving well 434.

The second portion of electrical paths 452, 454 and 456 exposed by sample receiving well 434 create at least a working electrode W, a blank electrode B and at least a reference/counter electrode R. A first reagent mixture 470 contains the mixture previously described for the working electrode that is disposed on the working electrode W. A second reagent mixture 472 contains the mixture previously described for the blank electrode that is disposed on the blank electrode B. The reference/counter electrode R may contain any reference material 474 previously disclosed. In this embodiment of the present invention, sample receiving well 434 serves as both the sample inlet and the sample chamber for receiving a fluid sample such as blood for the determination of an analyte in the blood sample.

It should be understood that the conduit paths in any of the embodiments disclosed herein may be made from any non-corroding metal. Carbon deposits such as for example carbon paste or carbon ink may also be used as the conduit paths, all as is well known by those of ordinary skill in the art.

Chemical Reagents
Enzyme

The disposable biosensor of the present invention includes at least a chemical agent in the reagent matrix of the working electrode W that consumes the analyte to be measured depending on the dehydrogenase enzyme used in the reagent matrix. For a non-limiting example, an alcohol dehydrogenase would be used when the analyte to be measured is ethanol. Another non-limiting example would be glutamate dehydrogenase when the analyte to be measured is glutamate. The blank electrode would be essential in the present invention for making an accurate determination of the concentration of alcohol in a body fluid if the blood sample contains interferants. As previously explained, the use of such a blank electrode helps to distinguish the oxidation current caused by ethanol from the oxidation current caused by other oxidizable species in the sample fluid. Continuing with the alcohol example, a commercially available alcohol dehydrogenase from Sigma Chemical Company, St. Louis, MO, or From Worthington Biochemical Corporation, Lakewood, NJ is used for the preparation of the alcohol working electrode. The concentration of, for example, alcohol dehydrogenase in the reagent mixture is in the range of 5 mg/ml to 100 mg/ml, preferably in the range of 10 mg/ml to 50 mg/ml, and more preferably in the range of 20 mg/ml to 40 mg/ml.

Diaphorase

Diaphorase is an essential part of the reagent matrix for the working electrode. Diaphorase is an enzyme of the flavoprotein type and is capable of oxidizing a reduced form of the co-enzyme NAD. The concentration of diaphorase in the reagent matrix is in the range of 2 mg/ml to 50 mg/ml, preferably in the range of 5 mg/ml to 20 mg/ml.

Chemically Oxidizing Reagents

Chemically oxidizing reagents such as redox mediators are included in the disposable biosensor. It is preferable to use a redox mediator in its oxidized form. It is also desirable that the reduced form of the mediator is capable of being oxidized electrochemically at the electrode surface at the applied potential. It is further desirable that the mediator is stable in the reagent matrix. When used in a reference electrode, it is still further desirable that the mediator can make the reference electrode function properly. The redox mediator can be selected from, but not limited to, various metal compounds and organic redox compounds. Examples of acceptable redox mediators include potassium (or sodium) ferricyanide, ferrocene and its derivatives, cupric compounds, nitrite compounds, ruthenium compounds such as hexaammineruthenium(III) chloride and its derivatives, and osmium complexes, 1,10-phenanthroline-5,6-dione, meldola's blue, Tetrathiafulvalene 7,7.8.8-tetracyanoquinodimethane, Tetrathiafulvalene, TCNQ, hydroquinone, dichlorophenoliondophenol, p-benoquinone, o-phenylenediamine, 3,4-dihydroxybenzaldehyde, and the like. The preferred mediator is potassium ferricyanide or hexaammineruthenium (III) chloride. The concentration of potassium ferricyanide in the reagent mixture is preferably in the range of 0.5% to 10%, preferably in the range of 1% to 5%, and more preferably in the amount of 3% (w/w) of the reagent mixture. The concentration of hexaammineruthenium (III) chloride in the reagent mixture is preferably in the range of 0.5% to 5%, more preferably in the range of 1% to 2%.

Enzyme Co-Factor

The enzyme co-factor included in the reagent matrix of the disposable biosensor 10, 10', 430 is the organic cofactor nicotinamide adenine dinucleotide phosphate (NAD), which is used due to the use of dehydrogenase and diaphorase. The concentration of the co-factor in the reagent matrix is in the range of 0.1% to 2%, preferably in the range of 0.2 to 1%, and more preferably equal to 0.5% (w/w).

Polymers

The polymer used as the binder in the reagent matrix should be sufficiently water-soluble and should also be capable of stabilizing and binding all other chemicals in the reagent to the conductive surface layer in the electrode area. Suitable polymers include, but are not limited to, low and high molecular weight polyethylene oxide (PEO), polyethylene glycol, polyvinyl pyrolidone, starch, methylcellulose, hydroxypropylcellulose, polyvinyl alcohol (PVA), carboxy methyl cellulose (CMC), and polyamino acids. The reagent binder may be a single polymer or a combination of polymers preferable in a concentration range of about 0.02% (w/w) to about 7.0% (w/w). The preferred binder in the reagent matrix of the present invention is a combination of polyethylene oxide (PEO) and methylcellulose. PEO's molecular weight ranges from thousands to millions and is available from Scientific Polymer Products, NY, USA. The concentration of PEO in the reagent matrix is preferably about 0.04% (w/w) to about 2% (w/w). Methylcellulose, which is available under the brand name of Methocel 60 HG (Cat. No. 64655, Fluka Chemicals, Milwaukee, WI, USA) has a concentration in the reagent matrix preferably in the range of about 0.02% (w/w) to about 5% (w/w).

Surfactants

The surfactant may be optionally included in the reagent mixture to facilitate dispensing of the reagent mixture into the electrode areas. The surfactant also helps in quickly dissolving the dry chemical reagents when a sample fluid enters the sample channel of the disposable biosensor. The amount and type of surfactant is selected to assure the previously mentioned functions and to avoid a denaturing effect on the enzymes. Surfactants can be selected from, but are not limited to, various anionic, cationic, non-ionic, and zwitterionic detergents. Examples of acceptable surfactants are polyoxyethylene ether, Tween 20, sodium cholate hydrate, hexadecylpyridinium cholide monohydrate and CHAPs. The preferred surfactant is a polyoxyethylene ether. More preferably, it is t-octylphenoxypolyethoxyethanol and is available under the brand name Triton X-100.

The concentration of Triton X-100 in the reagent mixture is preferably about 0.01% (w/w) to about 2%.

Buffer

Optionally, a buffer may be present along with a redox mediator in dried form in the sensor strip of the present invention. The buffer is present in a sufficient amount so as to substantially maintain the pH of the reagent mixtures. Examples of suitable buffers include citric acid, phosphates, Tris, and the like. In the present invention, the pH of the buffer is preferably in the range from about 5.0 to about 8.5.

Bulking Reagent

An optional bulking agent that is water soluble and an inactive ingredient is preferably added into the reagent mixture/matrix. The use of a bulking agent is advantageous when an electrode forming layer is used to contain the reagent matrix such that the electrode openings in the electrode forming layer will not trap bubbles when a sample fluid fills the capillary channel. Various sugars such as, for example, trehalose, galactose, glucose, sucrose, lactose, mannitol, mannose, fructose, sucrose, lactose, lactitol, sorbitol, xylitol, nicotinamide, maltose, and the like, can be added into the reagent mixture as long as they do not react with other ingredients and are inactive at the electrode surface. The bulking agent can be one chemical or a combination of chemicals. The amount of bulking agent in the reagent mixture is in the range from about 1% to about 15% (w/w).

Making the Biosensor

As can be inferred from the description above, the disposable electrochemical biosensor based on NAD(P)-dependent dehydrogenase and diaphorase is made as follows.

The base layer 20 with the conductive layer 21 is formed and scribed as described previously. The channel forming layer 40 is formed as described above and laminated to the base layer 20. A predefined amount of the first reagent is disposed onto the working electrode portion 20W and dried to form the working electrode W. A predefined reference material is disposed onto the reference electrode portion 20R forming the reference electrode R. In the case where the reference uses reference electrode reagent, a predefined amount of the reference reagent is disposed onto the reference electrode portion 20R and dried. After the working electrode W and reference electrode R are formed, the cover layer 50 is then laminated to the channel forming layer 40 such that the channel notch 42 is positioned such that the working electrode W and the reference electrode R are positioned within the channel notch 42 and the vent opening 52 such that it at least partially overlays a portion of the channel notch 42.

In the embodiment where a reagent holding layer 30 is included, the reagent holding layer 30 is disposed directly onto the conductive layer 21 of the base layer 20 such that the through openings 32, 34, and optionally 36 expose working electrode portion 20W, reference electrode portion 20R, and optionally, blank electrode portion 20B. A predefined amount of the first reagent is disposed into through opening 32 and dried to form the working electrode W. A predefined reference material is disposed into the through opening 34 forming the reference electrode R. In the case where the reference uses reference electrode reagent, a predefined amount of the reference reagent is disposed into the through opening 34 and dried. Thereafter, the channel forming layer 40 is laminated to the reagent holding layer 30 such that the through openings 32, 34, and optionally 36 reside within the channel notch 42. Cover layer 50 is then laminated to channel forming layer 40 as previously described.

Determination of Alcohol in a Blood Sample

Notwithstanding the below example provides data for determining alcohol in a blood sample, it should be understood by those of ordinary skill in the art as previously disclosed that other analytes in the blood such as glutamate, glucose, lactate, cholesterol, hydroxybutyrate, glycerol, malate, leucine, and the like can also be determined using the appropriate dehydrogenase and diaphorase such that these disposable biosensors will also have the advantages previously disclosed.

For an alcohol biosensor, the underlying chemical reactions that occur when a blood sample containing alcohol (in the illustrative case, the alcohol is ethanol) are as follows.

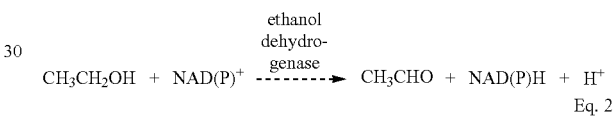

Eq. 1

$$CH_3CH_2OH + NAD(P)^+ \xrightarrow{\text{ethanol dehydrogenase}} CH_3CHO + NAD(P)H + H^+$$

Eq. 2

$$NAD(P)H + H^+ + Med_{ox} \xrightarrow{\text{diaphorase}} NAD(P)^+ + Med_{red}$$

Eq. 3

$$Med_{red} - e \xrightarrow{\text{electrode}} Med_{ox}$$

where $Med_{ox}$ is the oxidized form of the mediator, $Med_{red}$ is the reduced form of the mediator, and e represents the electron that generates the current at the electrode surface.

The biasing potential across the working electrode and the reference electrode for the alcohol biosensor is in the range of 100 my to 500 mv, preferably in the range of 300 mV to 400 mV. The voltage value in the range is not critical but it must be constant. The biasing potential across the working electrode and the reference electrode causes the mediator to change from a reduced state to an oxidized state at the electrode surface (See Eq. 3) and thereby generates the current based on the concentration of alcohol in the blood.

The concentration values of the blood samples for alcohol were obtained using a blood analyzer known as the Dimension RxL Chemistry Analyzer, which is sold by Siemens Healthcare Diagnostics, Inc. in Tarrytown, NY. The test data from the analyte test strips were obtained using a CH Instruments Potentiostat, model no. CHI 812B or model no. CHI 660A.

Test Data for Alcohol Determination Using Alcohol Biosensor with Diaphorase and $K_3Fe(CN)_6$ as the Mediator in the Reagent Matrix To determine the linearity response between the blood alcohol concentrations and the response based on the alcohol biosensor, the tests used 9 different concentration levels of ethanol. The levels are 0%, 0.01%, 0.02%, 0.04%, 0.08%, 0.12%, 0.16%, 0.2%, and 0.25%. Samples were prepared for these ethanol levels and current measurements were performed for each ethanol concentration. For each measurement, a new alcohol biosensor strip was used. Table 1 illustrates the test data obtained for the determination of alcohol where the ethanol biosensor has a working electrode reagent matrix that includes ethanol dehydrogenase, diaphorase, and an oxidized form of a redox mediator. The oxidized form of the redox mediator is potassium ferricyanide mediator.

TABLE 1

| alcohol concentration (%) | Response current (uA) |
|---|---|
| 0 | 0 |
| 0.01 | 0.095 |
| 0.02 | 0.185 |
| 0.04 | 0.397 |
| 0.08 | 0.809 |
| 0.12 | 1.214 |
| 0.16 | 1.538 |
| 0.2 | 1.847 |
| 0.25 | 2.259 |

Figure 7:
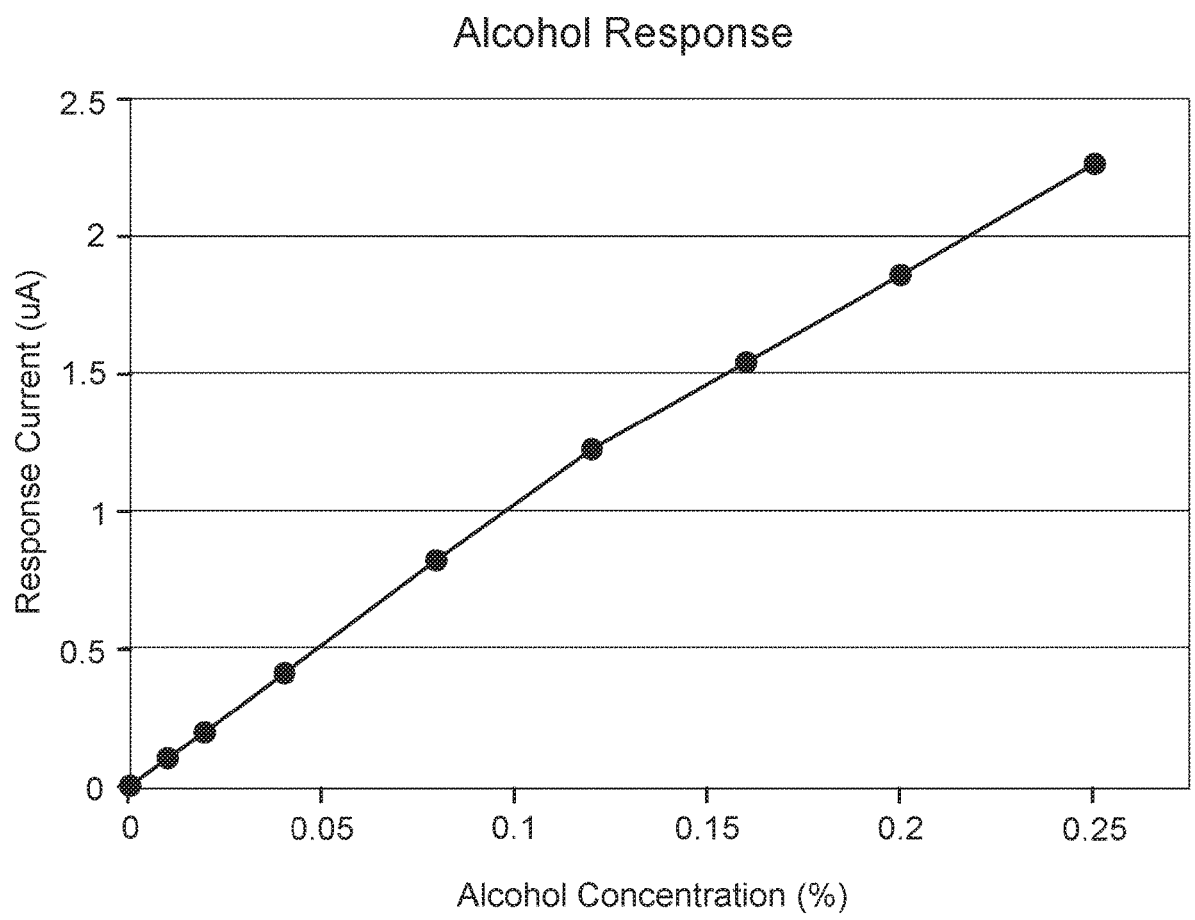
FIG. 7 is a graphic representation of the data in Table 1 showing the results for the alcohol biosensor current versus alcohol concentration using an alcohol biosensor incorporating the hydrogenase, the diaphorase and the oxidized form of the redox mediator potassium ferricyanide.

FIG. 7 shows the measured current response of the working electrode (i.e. ethanol dehydrogenase-based electrode) to varying alcohol concentrations. The current response is linear to the ethanol concentration throughout the alcohol concentration range tested.

Test Data for Alcohol Determination Using Alcohol Biosensor with Diaphorase and Hexamine-Ruthenium (III) Chloride as the Mediator in the Reagent Matrix The same levels and number of alcohol concentrations were used in this example as in the previous example with the exception of one higher concentration level. That is, the levels are 0%, 0.01%, 0.02%, 0.04%, 0.08%, 0.12%, 0.16%, 0.2%, 0.25%, and 0.35%. Samples were prepared for these ethanol levels and current measurements were performed for each ethanol concentration. For each measurement, a new alcohol biosensor strip was used. Table 1 illustrates the test data obtained for the determination of alcohol where the ethanol biosensor uses a hexamine-ruthenium (III) chloride mediator.

TABLE 2

| alcohol concentration (%) | Response current (uA) |
|---|---|
| 0 | 0 |
| 0.01 | 0.106 |
| 0.02 | 0.198 |
| 0.04 | 0.412 |
| 0.08 | 0.861 |
| 0.12 | 1.225 |
| 0.16 | 1.598 |
| 0.2 | 2.034 |
| 0.25 | 2.493 |
| 0.35 | 3.354 |

Figure 8:
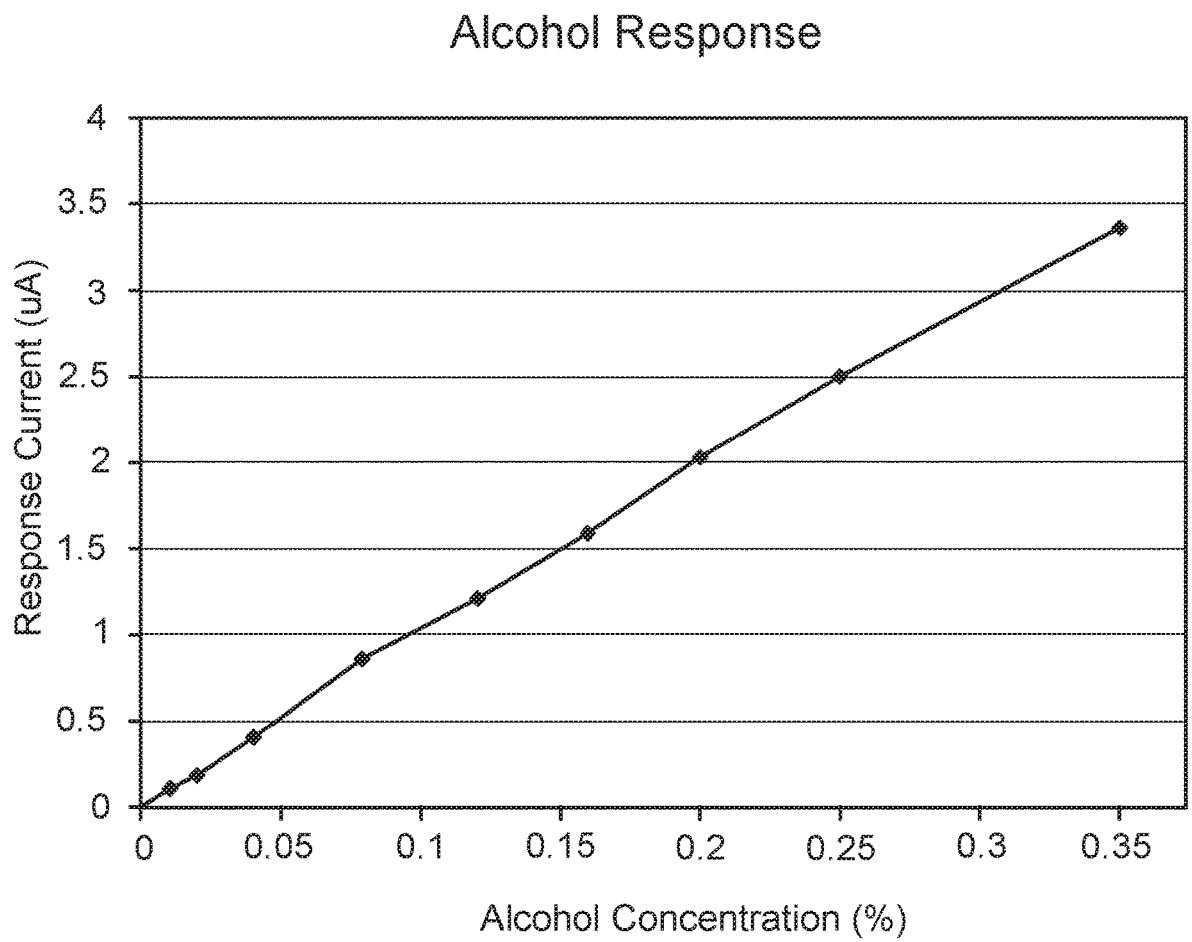
FIG. 8 is a graphic representation of the data in Table 2 showing the results for the alcohol biosensor current versus alcohol concentration using an alcohol biosensor incorporating the hydrogenase, the diaphorase and the oxidized form of the redox mediator hexamine-ruthenium (III) chloride.

FIG. 8 shows the measured current response of the working electrode (i.e. ethanol dehydrogenase-based electrode) to varying alcohol concentrations. The current response is linear to the ethanol concentration throughout the alcohol concentration range tested.

Precision Test Results for the Ethanol Biosensor Using Diaphorase with $K_3Fe(CN)_6$ as the Mediator in the Reagent Matrix To determine the precision response of the ethanol biosensor, this test used 2 different concentration levels of ethanol. The levels are 0.05% and 0.18%. Samples were prepared for these ethanol levels and current measurements were performed for each ethanol concentration. For each concentration level measurement, twenty new alcohol biosensors strip were used. Table 3 illustrates the test data obtained for the determination of alcohol where the ethanol biosensor uses diaphorase and a potassium ferricyanide mediator.

TABLE 3

| alcohol concentration | Response Current (uA) | |
|---|---|---|
| | 0.05% | 0.18% |
| 1 | 0.541 | 1.702 |
| 2 | 0.552 | 1.758 |
| 3 | 0.546 | 1.788 |
| 4 | 0.537 | 1.695 |
| 5 | 0.547 | 1.685 |
| 6 | 0.552 | 1.728 |
| 7 | 0.539 | 1.739 |
| 8 | 0.531 | 1.744 |
| 9 | 0.544 | 1.688 |
| 10 | 0.557 | 1.691 |
| 11 | 0.532 | 1.705 |
| 12 | 0.546 | 1.724 |
| 13 | 0.557 | 1.693 |
| 14 | 0.537 | 1.726 |
| 15 | 0.541 | 1.784 |
| 16 | 0.546 | 1.688 |
| 17 | 0.553 | 1.728 |
| 18 | 0.534 | 1.689 |
| 19 | 0.547 | 1.724 |
| 20 | 0.529 | 1.736 |
| mean | 0.543 | 1.721 |
| CV % | 1.55 | 1.81 |

Figure 9:
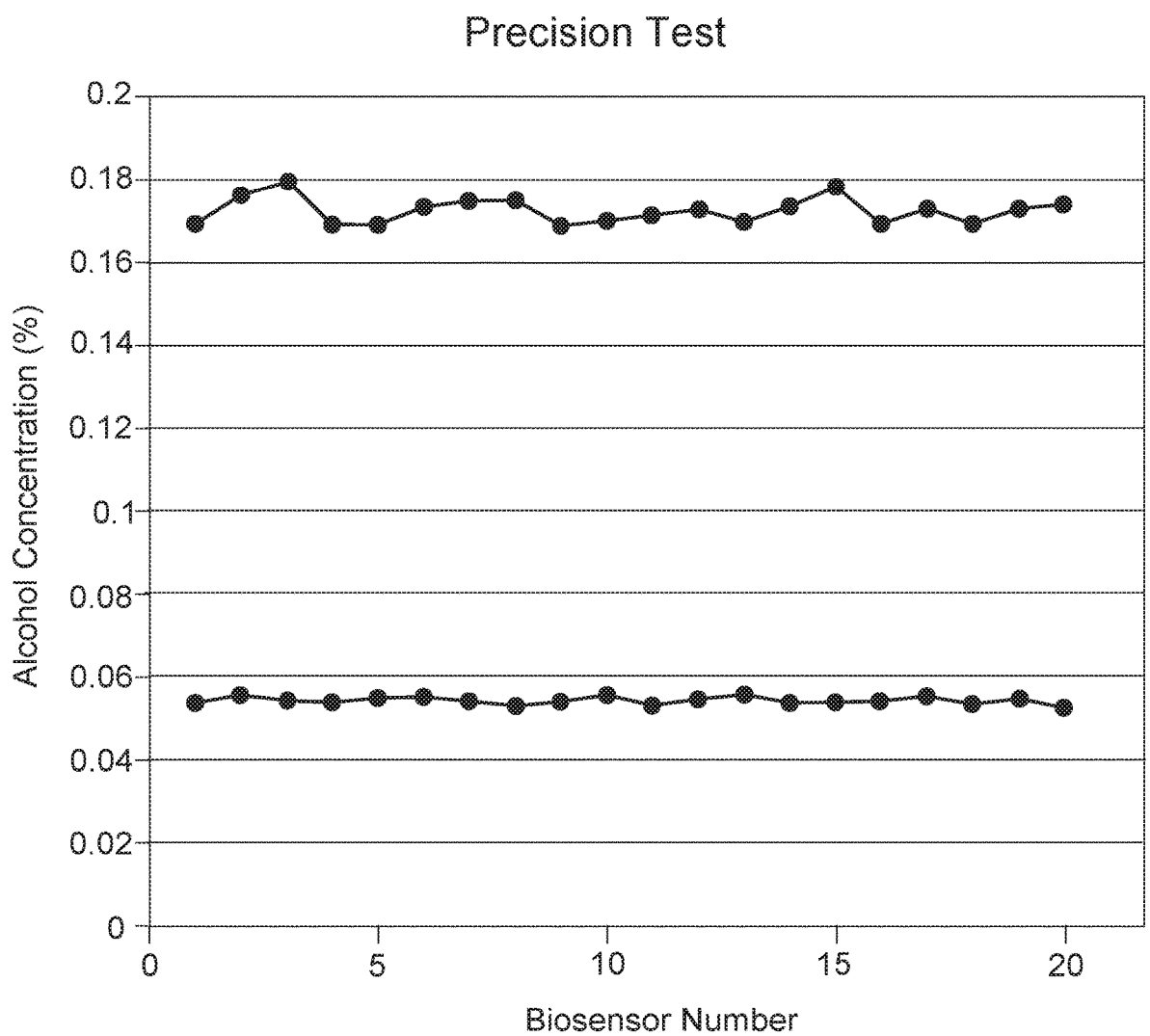
FIG. 9 is a graphic representation of the data in Table 3 showing the precision test results for the alcohol biosensor incorporating the hydrogenase, the diaphorase and the oxidized form of the redox mediator potassium ferricyanide.

FIG. 9 illustrates the measured current response of the working electrode (i.e. ethanol dehydrogenase-based electrode) to two alcohol concentrations. The mean of the 20 ethanol biosensors for each alcohol concentration is 0.543 and 1.721, respectively. The coefficient of variation in percent is 1.55 and 1.81, respectively. The test data indicates that the response from one alcohol biosensor to another is relatively precise.

Response Comparison of Alcohol Biosensors Between Oxidized Mediator and Reduced Mediator To determine the sensitivity response between the blood alcohol concentrations and the response based on (1) an alcohol biosensor using diaphorase and an oxidized form of a redox mediator and (2) an alcohol biosensor using a reduced form of the redox mediator and no diaphorase, the tests used 9 different concentration levels of ethanol. The levels are 0%, 0.01%, 0.02%, 0.04%, 0.08%, 0.12%, 0.16%, 0.2%, and 0.25%. As before the oxidized mediator used in one set of alcohol biosensors was potassium ferricyanide. The reduce mediator in the comparison set of alcohol biosensor was the reduced form of 1,10-phenanthroline-5,6-dione.

For an alcohol biosensor having the reduced form of the redox mediator 1,10-phenanthroline-5,6-dione and no diaphorase, the underlying chemical reactions that occur when a blood sample containing alcohol (in the illustrative case, the alcohol is ethanol) are as follows.

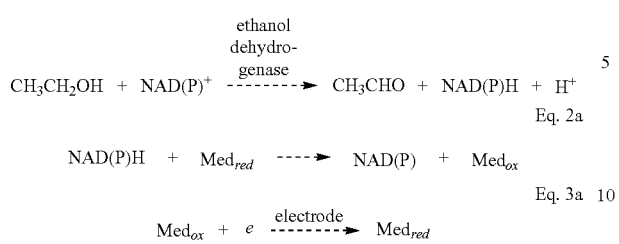

$$CH_3CH_2OH + NAD(P)^+ \xrightarrow{\text{ethanol dehydrogenase}} CH_3CHO + NAD(P)H + H^+ \quad \text{Eq. 1a}$$

$$NAD(P)H + Med_{red} \longrightarrow NAD(P) + Med_{ox} \quad \text{Eq. 2a}$$

$$Med_{ox} + e \xrightarrow{\text{electrode}} Med_{red} \quad \text{Eq. 3a}$$

where $Med_{ox}$ is the oxidized form of the mediator and $Med_{red}$ is the reduced form of the mediator.

The biasing potential across the working electrode and the reference electrode for this reduced form of redox mediator without diaphorase alcohol biosensors is in the range of −50 my to −300 mv, preferably in the range of −100 mV to −200 mV. The voltage value in the range is not critical but it must be constant. The biasing potential across the working electrode and the reference electrode causes the mediator in the comparison set to change from an oxidized state to a reduced state at the electrode surface (See Eq. 3a) and thereby generates the current based on the concentration of alcohol in the blood.

Samples were prepared for the above-referenced ethanol levels and current measurements were performed for each ethanol concentration for each biosensor set. For each measurement, a new alcohol biosensor was used. Table 4 illustrates the response comparison test data obtained for the determination of alcohol using the different sets of ethanol biosensors described above.

TABLE 4

| alcohol concentration (%) | Response current (uA) | |
|---|---|---|
| | no diaphorase reduced mediator | diaphorase oxidized mediator |
| 0 | 0 | 0 |
| 0.01 | 0.042 | 0.095 |
| 0.02 | 0.097 | 0.185 |
| 0.04 | 0.204 | 0.397 |
| 0.08 | 0.399 | 0.809 |
| 0.12 | 0.498 | 1.214 |
| 0.16 | 0.601 | 1.538 |
| 0.2 | 0.712 | 1.847 |
| 0.25 | 0.802 | 2.259 |

Figure 10:
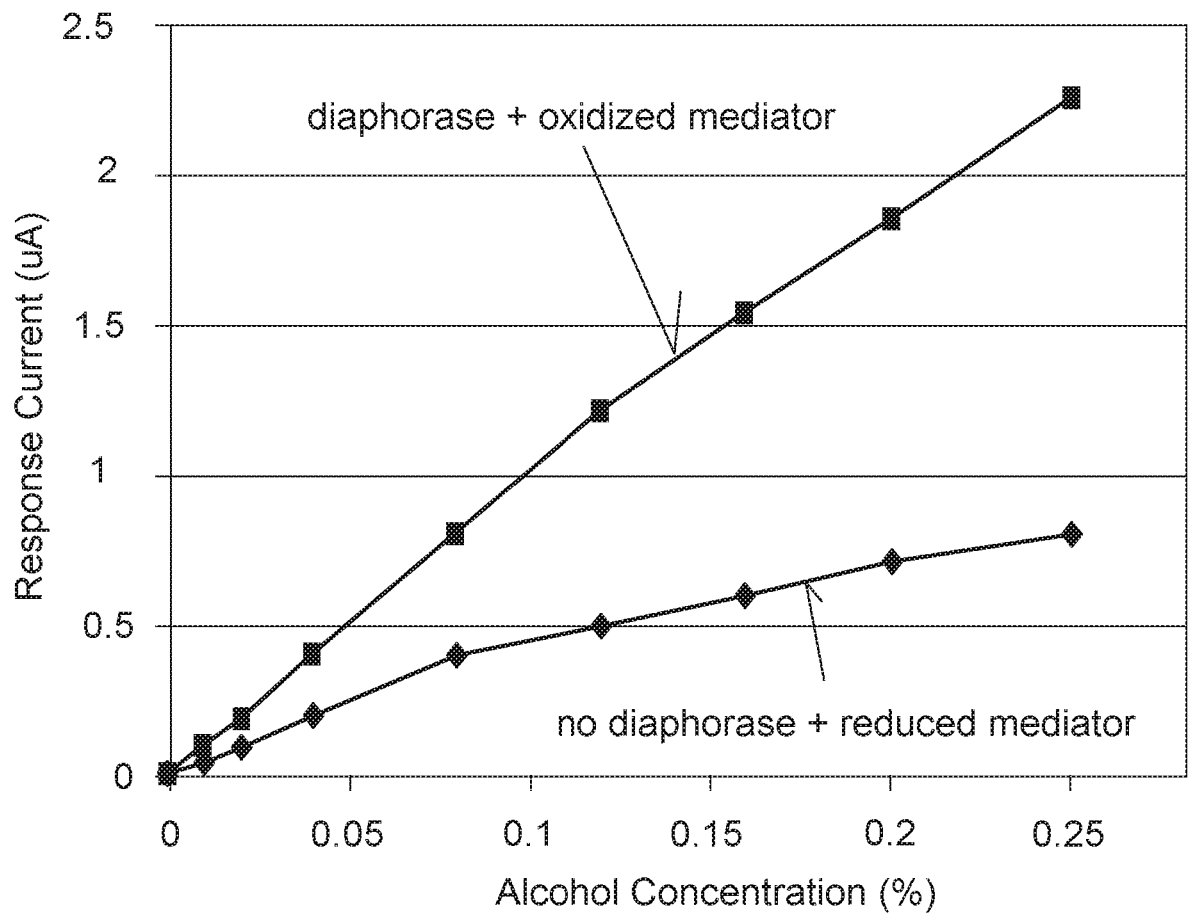
FIG. 10 is a graphic representation of the data in Table 4 showing the comparison of results for alcohol biosensors containing the hydrogenase, the diaphorase and the oxidized redox mediator potassium ferricyanide versus alcohol biosensors containing hydrogenase, no diaphorase and the reduced form of redox mediator 1,10-phenanthroline-5,6-dione.

FIG. 10 illustrates the measured current response of the working electrode (i.e. ethanol dehydrogenase-based electrode) to varying alcohol concentrations for each alcohol biosensor set. The current response is linear to the ethanol concentration throughout the alcohol concentration range tested for each alcohol biosensor set. The sensitivity, however, indicates a serious difference when using alcohol dehydrogenase with an oxidized form of the mediator and a reduced form of the mediator. As illustrated in the graph, the alcohol biosensor having the oxidized form of the mediator and diaphorase has a much more sensitive response from 0 to 2.6 microamps versus 0 to 0.8 microamps for the reduced form of the mediator and no diaphorase. Because the response is more sensitive, the accuracy of the measurement is also improved. From the above equations, the skilled artisan will recognize that when using the reduced form of the mediator, the presence of diaphorase would not effect the reactions since the reduced form of the mediator loses the electron to NAD(P)H to form NAD(P) and the oxidized form of the mediator.

Alcohol Biosensor Storage Stability

To determine the stability of an alcohol biosensor that includes a NAD(P)-dependent dehydrogenase, diaphorase and an oxidized form of a redox mediator and an alcohol biosensor using a reduced form of the redox mediator and no diaphorase, the comparison was performed on the alcohol biosensors over a period of twelve months. Each reading was taken with a new alcohol sensor on a sample having an ethanol concentration of 0.15%. As before the oxidized mediator used in one set of alcohol biosensors was potassium ferricyanide. The reduced form of the mediator in the comparison set of alcohol biosensors was the reduced form of 1,10-phenanthroline-5,6-dione.

The biasing potential across the working electrode and the reference electrode for alcohol biosensors with diaphorase and potassium ferricyanide as electron mediator is in the range of 100 my to 500 mv, preferably in the range of 300 mV to 400 mV. The biasing potential across the working electrode and the reference electrode for alcohol biosensors with reduced form of the redox mediator 1,10-phenanthroline-5,6-dione and no diaphorase is at the range of −50 mV to −300 mV, preferably in the range of −100 mV to −200 mV.

Samples were prepared for the above-referenced ethanol levels and current measurements were performed for the concentration of 0.15% for each biosensor set. For each measurement, a new alcohol biosensor was used. Table 5 illustrates the response comparison test data obtained for the determination of alcohol using the different sets of ethanol biosensors described above.

TABLE 5

| | response current (uA) | |
|---|---|---|
| Time | diaphorase with oxidized mediator | no diaphorase with reduced mediator |
| 0 months | 1.378 | 0.577 |
| 1 month | 1.384 | 0.583 |
| 2 months | 1.379 | 0.564 |
| 4 months | 1.389 | 0.571 |
| 6 months | 1.392 | 0.552 |
| 8 months | 1.377 | 0.517 |
| 10 months | 1.386 | 0.489 |
| 12 months | 1.391 | 0.398 |

Figure 11:
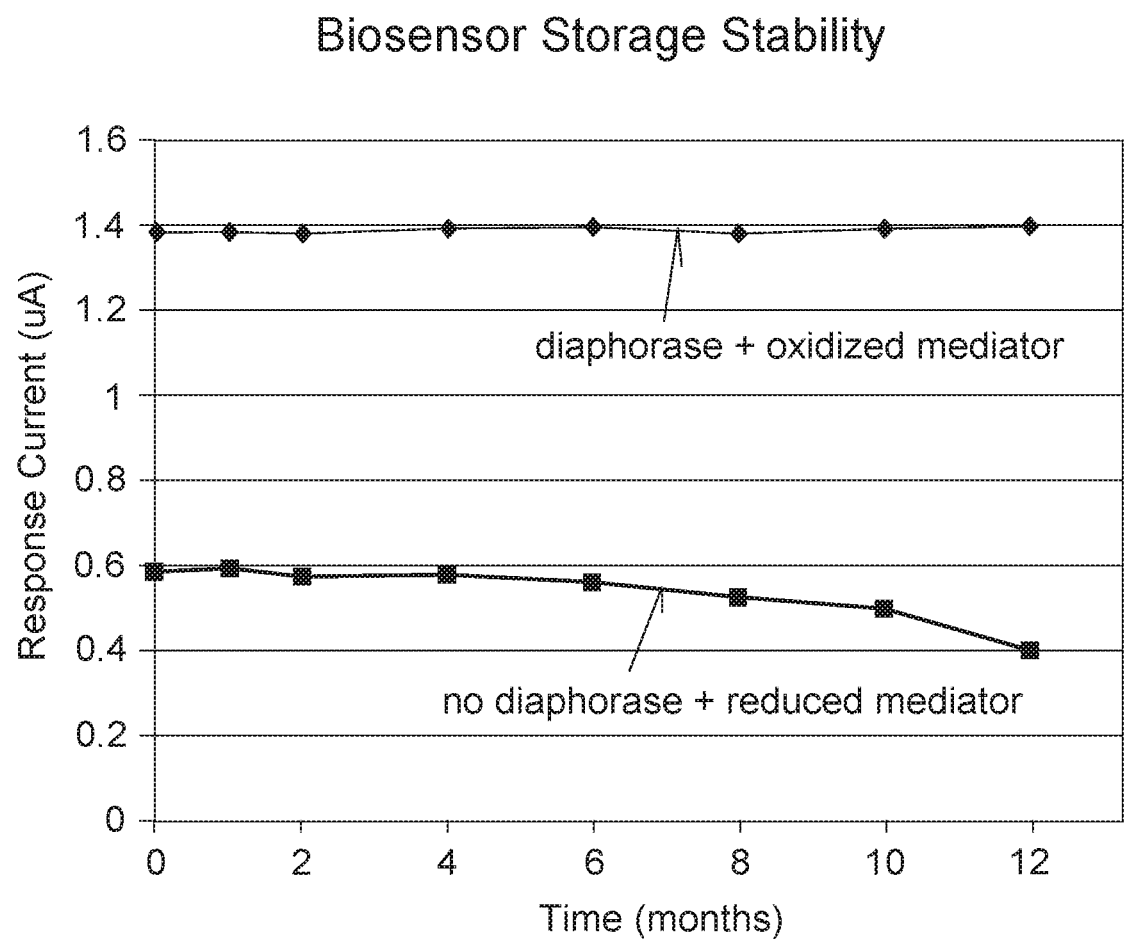
FIG. 11 is a graphic representation of the data in Table 5 showing the long term storage stability for alcohol biosensors containing the hydrogenase, the diaphorase and the oxidized redox mediation potassium ferricyanide versus alcohol biosensors containing hydrogenase, no diaphorase and the reduced form of the redox mediator 1,10-phenanthroline-5,6-dione.

FIG. 11 illustrates the measured current response of the working electrode (i.e. ethanol dehydrogenase-based electrode) under ambient storage conditions for each alcohol biosensor set. The current response is stable to the ethanol concentration throughout the 12-month time period for the alcohol biosensor set having the NAD(P)-dependent dehydrogenase, the oxidized form of the redox mediator and diaphorase. As seen in the graphical illustration and in Table 5 above, the current response decreases throughout the 12-month time period for the alcohol biosensor set having the reduced form of the redox mediator and no diaphorase. In fact, it is apparent that, after the $4^{th}$ month of storage the alcohol biosensors having the reduce form of the redox mediator and no diaphorase, the current response begins to decrease and drops off more quickly the older the biosensor becomes. As illustrated in the graph, the alcohol biosensors having the reduced form of the mediator and no diaphorase decreases in response from 0.571 microamps at 4 months storage life (or an average of 0.574 microamps) to 0.398 microamps at 12 months storage life. In summary, the alcohol biosensors response decreases with age.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A disposable, single-use biosensor comprising:
   a sensing surface having at least a working electrode portion, a blank electrode portion, and a reference electrode portion;
   a first soluble reagent disposed on the working electrode portion containing a NAD(P)-dependent dehydrogenase, NAD(P)+, diaphorase, and an oxidized form of a redox mediator forming a working electrode;
   a second soluble reagent disposed on the blank electrode portion forming a blank electrode, wherein the second reagent and the first reagent differ in composition at least in that the second reagent does not contain dehydrogenase; and
   a reference electrode material disposed on the reference electrode portion forming a reference electrode;
   wherein the biosensor is configured such that the first soluble reagent dissolves while a sample fills a sample chamber of the biosensor, at least in part, by capillary action.

2. The disposable, single-use biosensor of claim 1, wherein the second soluble reagent contains NAD(P)+, diaphorase, and an oxidized form of a redox mediator disposed on the blank electrode portion forming the blank electrode.

3. The disposable, single-use biosensor of claim 1, wherein the reference electrode material is one of Ag—AgCl or a reference matrix containing at least a chemically oxidizing reagent selected from the group consisting of a reduced form of a redox mediator, an oxidized form of a redox mediator, and a mixture of a reduced form and an oxidized form of a redox mediator.

4. The disposable, single-use biosensor of claim 1, wherein the NAD(P)-dependent dehydrogenase is one of alcohol dehydrogenase, glutamate dehydrogenase, glucose dehydrogenase, lactate dehydrogenase, cholesterol dehydrogenase, D-3-hydroxybutyrate dehydrogenase, glycerol dehydrogenase, malate dehydrogenase, and leucine dehydrogenase.

5. The disposable, single-use biosensor of claim 1, wherein the oxidized form of the redox mediator includes metal compounds or organic redox compounds.

6. The disposable, single-use biosensor of claim 1, wherein the oxidized form of the redox mediator includes at least one of potassium ferricyanide, sodium ferricyanide, ferrocene and its derivatives, ruthenium compounds such as hexaamineruthenium(III) chloride and its derivatives, osmium complexes, 1,10-phenanthroline-5,6-dione, meldola's blue, Tetrathiafulvalene 7,7,8,8-tetracyanoquinodimethane, hydroquinone, dichlorophenoliondophenol, p-benzoquinone, o-phenylenediamine, and 3,4-dihydroxybenzaldehyde.

7. The disposable, single-use biosensor of claim 1, wherein the first soluble reagent further includes a polymer, a surfactant, and a buffer.

8. The disposable, single-use biosensor of claim 7, wherein the first soluble reagent further includes a bulking reagent.

9. The disposable, single-use biosensor of claim 2, wherein the second soluble reagent further includes a polymer, a surfactant, and a buffer.

10. The disposable, single-use biosensor of claim 9, wherein the second soluble reagent further includes a bulking reagent.

11. The disposable, single-use biosensor of claim 1, further comprising:
   a base layer made of an electrically-insulating material with at least two electrical circuits delineated thereon, each of the at least two electrical circuits extending longitudinally along the base layer, wherein each of the at least two circuits has an electrically-conductive contact pad formed at each of a base layer proximal end portion and a base layer distal end portion with an electrically-conductive trace electrically coupling the electrically-conductive contact pad at the base layer proximal end portion with the corresponding electrically-conductive pad at the base layer distal end portion, wherein one electrically-conductive pad at the base layer distal end portion forms the working electrode and the other of the electrically-conductive pad at the base layer distal end portion forms the reference electrode;
   a channel forming layer made of an electrically-insulating material disposed on the base layer, the channel forming layer having a slot that extends from a channel layer distal end a predefined distance sufficient to expose each electrically-conductive pad at the base layer distal end portion, the channel forming layer having a shorter length than the length of the base layer so that each electrically-conductive pad at the base proximal end portion is exposed; and
   a cover layer made of an electrically-insulating material disposed over the channel forming layer creating the sample chamber with the slot of the channel forming layer, the cover layer having a vent opening spaced from a cover layer distal end, wherein the vent opening at least partially communicates with the sample chamber.

12. The disposable, single-use biosensor of claim 11 further comprising a reagent holding layer between the base layer and the channel forming layer, the reagent holding layer having at least two through openings at a reagent holding layer distal end, wherein one of the at least two through openings coincides with the working electrode and the other of the at least two through openings coincides with the reference electrode.

13. The disposable, single-use biosensor of claim 11, wherein the base layer has a third electrical circuit extending longitudinally along the base layer, wherein the third electrical circuit has an electrically-conductive contact pad formed at each of the base layer proximal end portion and the base layer distal end portion with an electrically-conductive trace electrically coupling the electrically-conductive contact pad at the base layer proximal end portion with the corresponding electrically-conductive pad at the base layer distal end portion forming the blank electrode, wherein the blank electrode is within the slot of the channel forming layer.

14. The disposable, single-use biosensor of claim 13, wherein the reagent holding layer has a third through opening, wherein the third through opening coincides with blank electrode.

15. A method of making a disposable, single-use biosensor based on NAD(P)-dependent dehydrogenase and diaphorase, the method comprising:

providing a sensing surface having at least a working electrode portion, a blank electrode portion, and a reference electrode portion;

disposing a first soluble reagent on the working electrode portion, the first soluble reagent containing a NAD(P)-dependent dehydrogenase, NAD(P)+, diaphorase, and an oxidized form of a redox mediator and drying the first soluble reagent forming a first electrode matrix creating a working electrode, wherein the biosensor is configured such that the first soluble reagent dissolves while a sample fills a sample chamber of the biosensor, at least in part, by capillary action;

disposing a second soluble reagent on the blank electrode portion, wherein the second soluble reagent and the first soluble reagent differ in composition at least in that the second soluble reagent does not contain dehydrogenase; and disposing a reference electrode material on the reference electrode portion forming a reference electrode, wherein the reference electrode material is one of Ag—AgCl or a reference electrode reagent containing at least a chemically oxidizing reagent selected from the group consisting of a reduced form of a redox mediator, an oxidized form of a redox mediator and a mixture of a reduced form and an oxidized form of a redox mediator and drying the reference electrode reagent forming a reference electrode matrix.

16. The method of claim 15, wherein the first soluble reagent comprises:

0.1 grams to 0.5 grams of the NAD(P)-dependent dehydrogenase;
0.02 grams to 0.1 grams of the NAD(P)+;
0.02 grams to 0.5 grams of the diaphorase.

17. The method of claim 15, wherein the first soluble reagent comprises:

0.2 grams to 0.4 grams of the NAD(P)-dependent dehydrogenase;
0.05 grams of the NAD(P)+;
0.05 grams to 0.2 grams of the diaphorase; and
0.3 grams of the oxidized form of a redox mediator.

18. The method of claim 15, wherein the second soluble reagent contains NAD(P)+, diaphorase, and an oxidized form of a redox mediator disposed on the blank electrode portion forming the blank electrode.

19. The method of claim 15, wherein at least one of:

the first soluble reagent includes a polymer, a surfactant, and a buffer;
the first soluble reagent includes a bulking reagent;
the second soluble reagent includes a polymer, a surfactant, and a buffer; and
the second soluble reagent includes a bulking reagent.

20. The disposable, single-use biosensor of claim 1, wherein the biosensor is configured such that the first soluble reagent is dissolved and in a solution phase during measurement of the sample.

21. The method of claim 15, wherein the biosensor is configured such that the first soluble reagent is dissolved and in a solution phase during measurement of the sample.

* * * * *

UNITED STATES PATENT AND TRADEMARK OFFICE
CERTIFICATE OF CORRECTION

PATENT NO. : 12,064,243 B2
APPLICATION NO. : 16/747720
DATED : August 20, 2024
INVENTOR(S) : Pei et al.

Page 1 of 1

It is certified that error appears in the above-identified patent and that said Letters Patent is hereby corrected as shown below:

In the Claims

At Column 20, after Line 4, Claim 16, "0.1 grams to 0.5 grams of the oxidized form of a redox mediator.", should be added.

Signed and Sealed this
Fourteenth Day of January, 2025

Derrick Brent
*Acting Director of the United States Patent and Trademark Office*